United States Patent [19]

Katz

[11] 4,327,743
[45] May 4, 1982

[54] DETECTION OF TEMPERATURE VARIATIONS OVER REGIONS OF LIVING TISSUE

[75] Inventor: Seymour Katz, Glen Cove, N.Y.

[73] Assignee: E-Z-EM Company, Inc., Westbury, N.Y.

[21] Appl. No.: 209,128

[22] Filed: Nov. 21, 1980

[51] Int. Cl.$^3$ ............................................. A61B 5/00
[52] U.S. Cl. .................................................. 128/736
[58] Field of Search ........................................ 128/736

[56] References Cited

U.S. PATENT DOCUMENTS

| | | | |
|---|---|---|---|
| 3,339,542 | 9/1967 | Howell | 128/736 |
| 3,533,399 | 10/1970 | Goldberg et al. | 128/736 |
| 4,060,654 | 11/1977 | Quenneville | 128/736 |
| 4,148,951 | 4/1979 | Clark | 128/736 |
| 4,186,731 | 2/1980 | Clark | 128/736 |

*Primary Examiner*—William E. Kamm
*Attorney, Agent, or Firm*—McAulay, Fields, Fisher, Goldstein & Nissen

[57] ABSTRACT

A first elastic film containing cholesteric liquid crystals and a second elastic protective film having different elasticities are attached to each other solely along the periphery of the two sheets. Differential air pressure applied across the dual film structure causes it to stretch and conform to the body tissues whose temperature variations are being studied. The liquid crystal containing film and the protective film stretch and adjust independently of one another, in response to differential pressure, to squeeze out any air in the space between the two sheets and to avoid puckering or other distortions. The protective film is in contact with the tissue being investigated and provides a barrier to protect the liquid crystals from contamination yet conveys the underlying temperature accurately to the liquid crystals.

7 Claims, 11 Drawing Figures

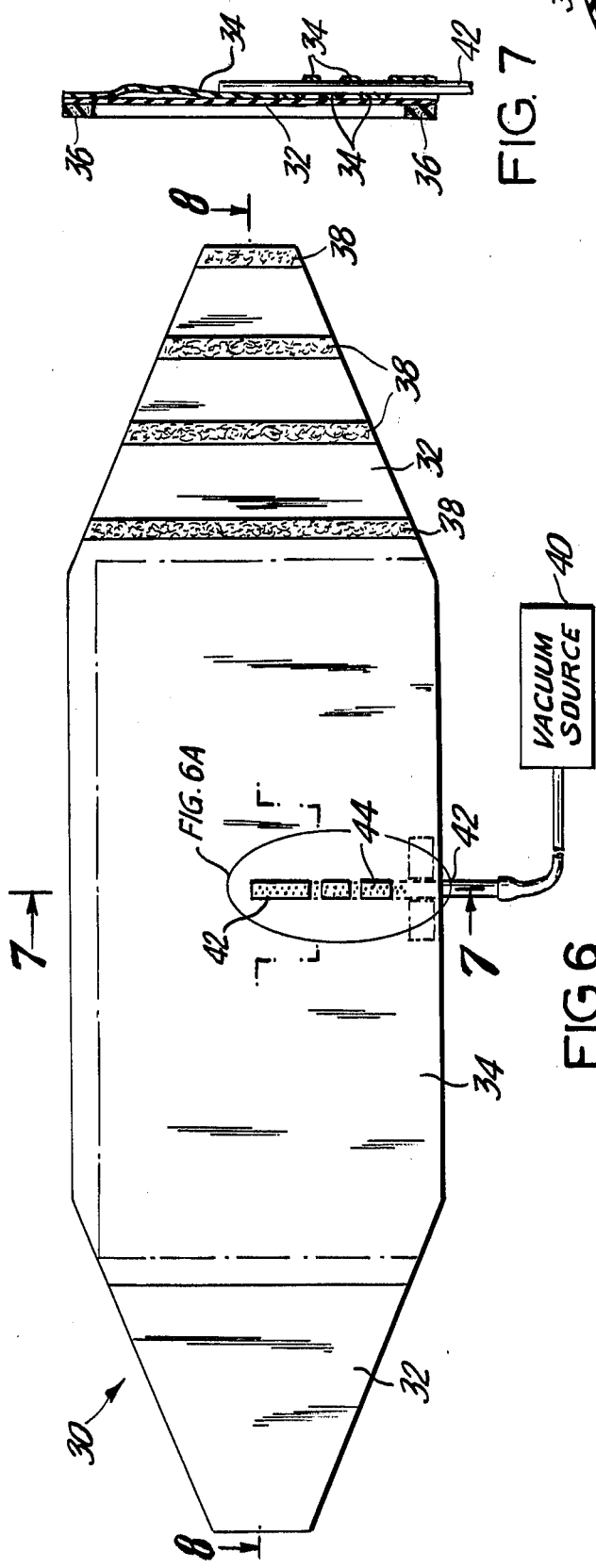
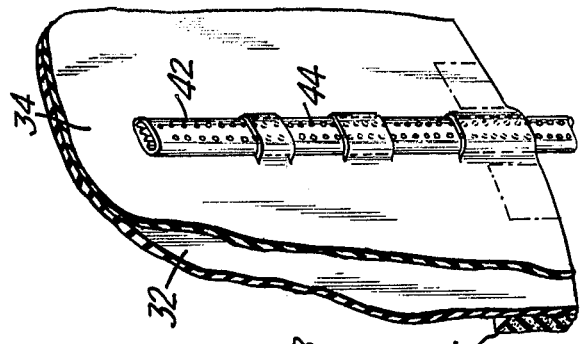
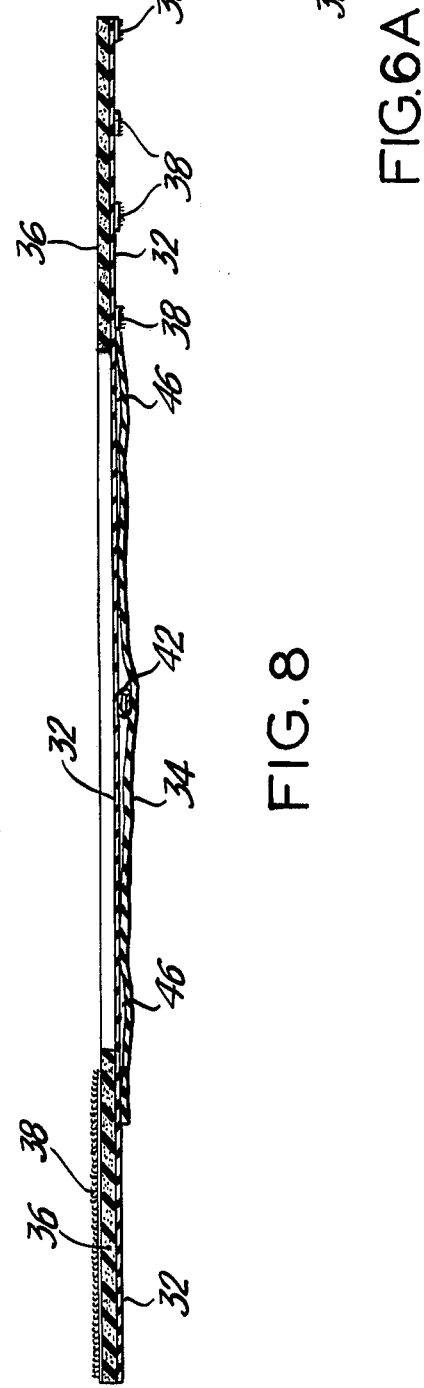

DETECTION OF TEMPERATURE VARIATIONS OVER REGIONS OF LIVING TISSUE

BACKGROUND OF THE INVENTION

This invention relates in general to the detection of relatively small temperature differentials or variations over selected regions of living tissue and more particularly to an improvement in the application of an elastomeric film containing cholesteric liquid crystals to the surface of the selected region of the body.

Techniques and apparatus for employing elastomer sheets of cholesteric liquid crystals (hereinafter generally liquid crystals) are described in the U.S. Pat. No. 4,135,497 issued Jan. 23, 1979 and in pending patent application Ser. No. 088,159 filed Oct. 25, 1979. The disclosure of this patent and patent application are incorporated herein by reference in order to simplify the specification herein.

Experience has shown that the skin oils from the tissues being investigated tend to migrate into the elastomeric film, react with the liquid crystals and cause degradation of the product. This is a key factor in limiting the number of times that any given unit of the products involved can be used.

Accordingly, it is a major purpose of this invention to provide a technique for reducing the contamination and degradation of the liquid crystals and thereby increase the usable life of the detection apparatus involved.

However, it is important that the liquid crystals remain in intimate thermal contact with the body tissues so as to continue to display relatively slight temperature differentials. Temperature differences of somewhat less than 0.1° C. can be visually identified by observing a color differential. It has been found that the least air bubble or interference with smooth continuous contact between the tissue being investigated and the elastomeric sheet will result in loss of meaningful picture over any portion of the tissue involved and/or loss of sensitivity.

Accordingly, it is important that any technique for reducing contamination be compatible with maintaining the sensitivity and reliability of the liquid crystal containing elastic sheet.

BRIEF DESCRIPTION

In brief, in one embodiment of this invention a chamber is inflated causing a liquid crystal containing elastic film and a protective elastic film to pillow outward. In another embodiment of this invention a vacuum is drawn causing a liquid crystal containing elastic film and a protective elastic film to be drawn back and thus forced back, against the tissue of a patient. In both cases, when a differential pressure is created, either by inflation or by the drawing of a vacuum, any air between the two films is forced out along the edges of the films. The liquid crystal containing film and the protective film are fastened to one another solely along their peripheries so that the two films are free to stretch and independently conform to any complex tissue shape impressed against the dual film structure. The protective film is positioned on the surface of the dual film structure that is applied to the patient's tissue being investigated thereby protecting the liquid crystal containing film from contamination due to body oils. The protective film is ¼ mm. thick and because it independently conforms to the tissue being investigated assures that the temperature differential along the surface of the patient's skin is sensed by the liquid crystals in the second film.

The protective film material is selected to be substantially more impervious to the skin oil than is the material of the liquid crystal containing film.

BRIEF DESCRIPTION OF THE DRAWINGS

FIG. 6 is an elevational view of a second embodiment of this invention in which the liquid crystal containing elastomer 32 and protective elastomer 34 are arranged in the form of a chest encircling device adapted for application to the measurement of surface temperature differentials over the breasts of a woman.

FIG. 6A is a perspective view of a portion of the inner end of the tube 42 showing the relationship between liquid crystal elastomer 32, protective elastomer 34 and tube 42. FIG. 6A is approximately the area encircled in FIG. 6.

FIG. 7 is a cross-sectional view along the plane 7—7 of the FIG. 6 device.

FIG. 8 is a cross-sectional view along the plane 8—8 of the FIG. 6 device.

DESCRIPTION OF THE PREFERRED EMBODIMENTS

Figure 1:
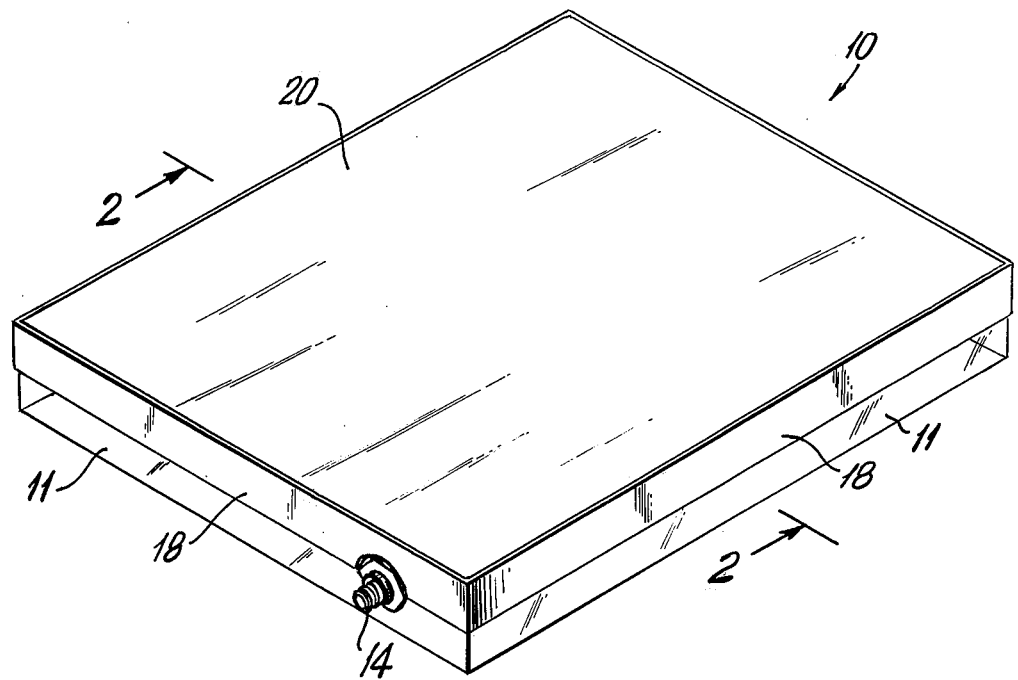
FIG. 1 is a perspective view of a first embodiment of this invention in which the liquid crystal elastomer 20 and protective elastomer 16 form one surface of an inflatable box.
Figure 2:
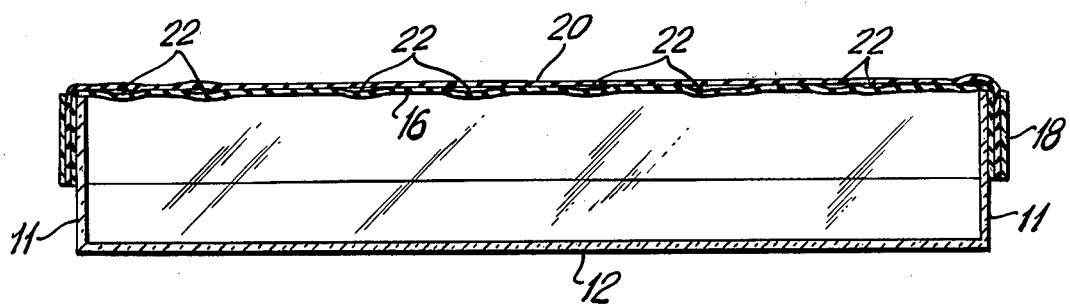
FIG. 2 is a cross-sectional view along the plane 2—2 through the FIG. 1 embodiment.

FIGS. 1 through 5 represent a first embodiment which corresponds to the embodiment disclosed in the referenced patent application, Ser. No. 088,159. FIGS. 6 through 10 represent a second embodiment that partially corresponds to the device disclosed in the referenced U.S. Pat. No. 4,135,497. Since the operation of these devices is disclosed in detail in the referenced patent and patent application, the description herein will only be sufficient to enable a clear understanding of the operation of the apparatus and the manner in which the improvement of this invention functions.

In the first embodiment there is shown a box 10 having side walls 11 and a base 12. A valve 14 extends out one of the side walls. It is through this valve 14 that the box is inflated. Rigid portions 11, 12 of the box are arranged so as to have an open top. Across this open top, and therefore defining the rest of the box, there is an elastic, liquid crystal containing film 16. This film 16 is folded over the rim of the box and cemented in position along its edges. On top of the liquid crystal containing elastic film 16 is a protective film 20.

The liquid crystals are contained within the film 16 and normally are enclosed between two layers of elastomeric film which, together with the liquid crystals, are fabricated so as to constitute a single sheet; specifically the film 16. The rubber elastomer involved in fabricating the film 16 is not highly impervious to the body oils. Accordingly, in use body oils migrate through the layers of the film 16 to react with and degrade the liquid crystals over a period of time and after a number of uses. The protective film 20 is also a rubber elastomer but is selected to have a density sufficiently great so that it is substantially impervious to migration of body oils. However, because the composition and density of the film 20 is substantially different from that of the film 16, these two films have different coefficients of elasticity (also called elastic modulus). Thus they will stretch in response to a given force and conform to a given shape in different fashions. It has been found that when these two film layers are bonded together or even tacked to one another across the surface of the two films, one film will tend to cause the other to pucker and/or to create air gaps. Accordingly, these two films 16 and 20 are adhered to or attached to one another solely around the edges thereof, and, even at that, not necessarily entirely around the edges.

Figure 3:
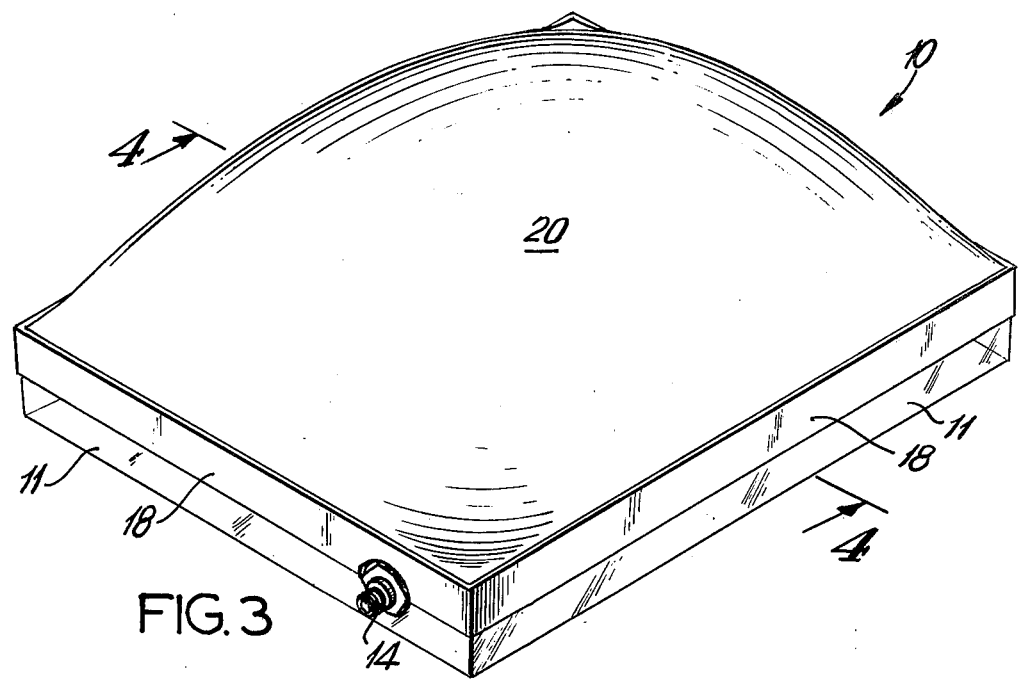
FIG. 3 is a view similar to that of FIG. 1 showing the device inflated.
Figure 4:
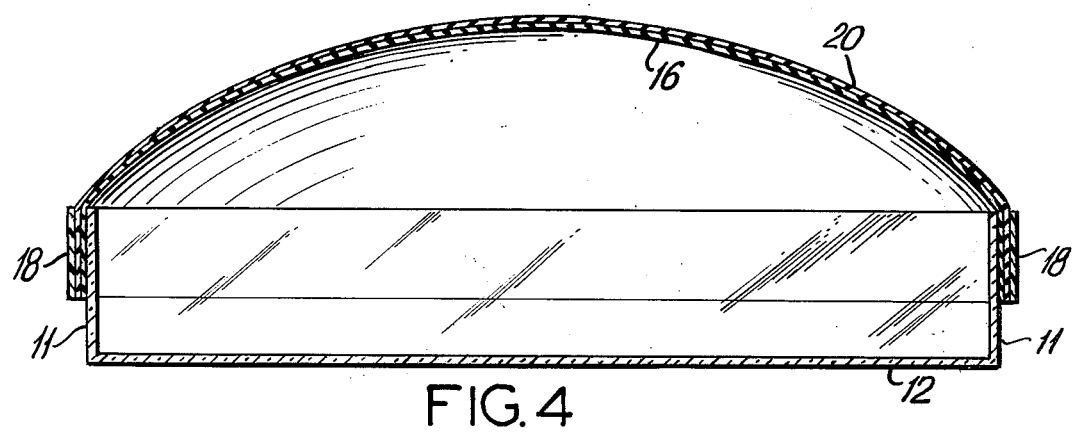
FIG. 4 is a cross-sectional view along the plane 4—4 through the FIG. 3 inflated device.

The protective film 20 is laid over the film 16 and folded around the corners of the box 10. The film 20 like the liquid crystal containing film 16, is cemented along its edges in place. The band 18 protects the edges of the two film 16, 20. The film 20 is not adhered to or attached in any way to the film 16 along the upper face of the box 10. Accordingly, there are small air spaces 22 that normally exist between the two films 16 and 20 when in the relaxed state. In use, air is pumped into the chamber within the box 10, through the valve 14, to cause the two elastic films 16 and 20 to inflate as shown in FIGS. 3 and 4. When inflated, the inner film 16 pillows outward pushing the outer film 20 before it. As a result, any air in the air spaces 22 is squeezed out from between the two films 16 and 20. So that the air in the spaces 22 can readily exit, it is important that the outer film 20 be tacked down to the box sidewall 11 at a plurality of spaced apart points. This will permit air to pass out from between the two films 16 and 20 into the atmosphere.

In this fashion the dual film structure 16, 20 when inflated will have no insulating air spaces between the two films. Yet each of the two films will be free to expand without being tacked down or tied down to the other film except along the band 18 edge.

Figure 5:
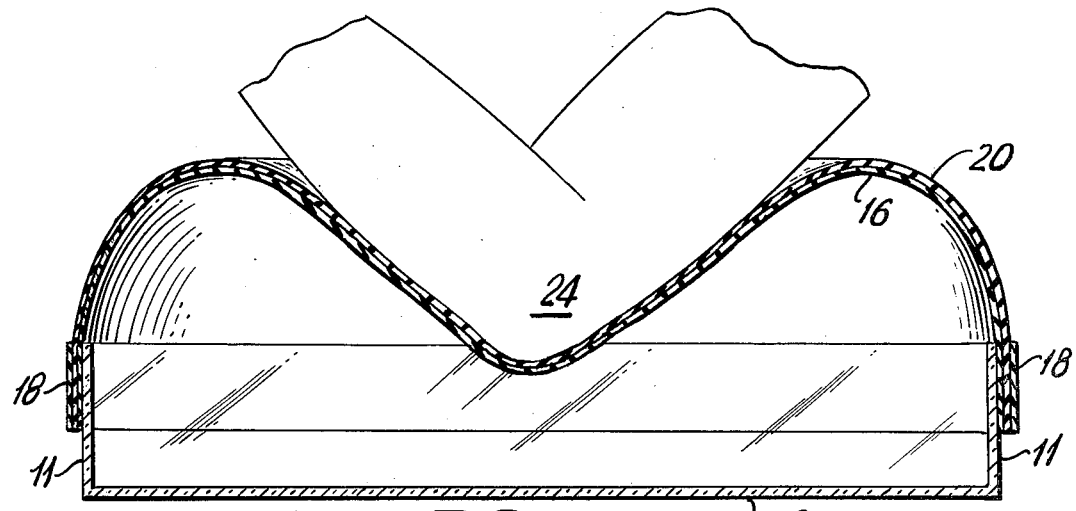
FIG. 5 illustrates the application of the inflated devices of FIGS. 3 and 4 to the elbow of a patient.

FIG. 5 illustrates a typical application of this embodiment in which an elbow 24 is pressed against the pillowed out dual elastic film structure. The inner film 20 is approximately ¼ mm. (10 mils.) thick and thus transmits the temperature of the adjacent tissue to the liquid crystals carried by the film 16. Because the film 20 as well as the film 16 is elastic, both will conform to the complex surface of the elbow 24 tissue and will provide intimate contact with the elbow area. As a result, the liquid crystals contained in the film 16 will provide a color pattern representative of any temperature variation over the surface of the elbow 24. In particular, injury to the elbow will normally be represented by a slight temperature rise. Since the liquid crystals are capable of indicating temperature differences of as little as 1/10° C., a color picture representing an abnormality will be provided.

For this color picture to be seen, it is essential that the base 12 of the box 10 be transparent and thus, in the embodiment shown, the side walls 11 and base 12 are made of a rigid transparent plastic material.

The second embodiment shown in FIGS. 6 through 10 may be termed a brassiere-like device in that it is adapted to be wrapped around the chest of a woman for the purposes of providing a thermographic representation of temperature variations across the breasts of a woman. This brassiere device 30 has a liquid crystal-containing elastic film 32 as an outer sheet and a protective film 34 as an inner sheet. This dual film 32, 34 structure is fastened on its top edge and two side edges, along the line 35, to a flexible resilient frame 36 made of material such as foam rubber.

Figure 9:
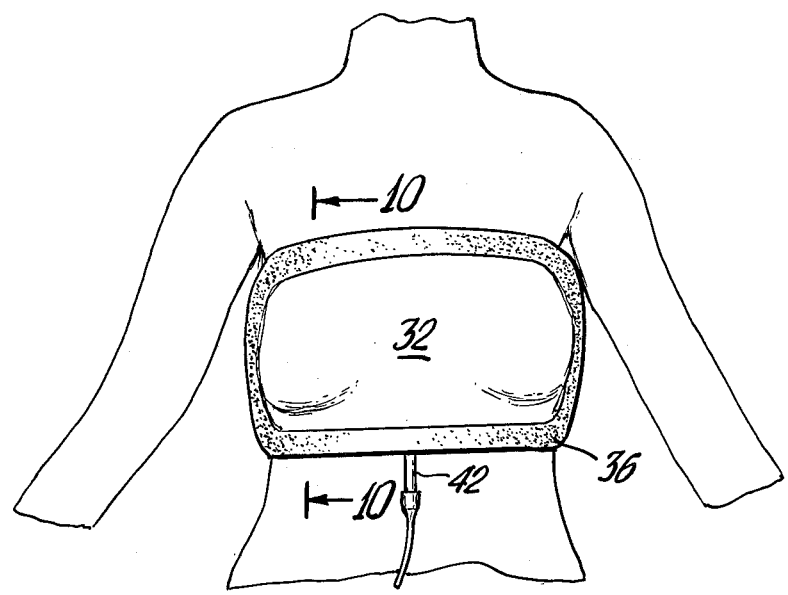
FIG. 9 is an elevational perspective view of the FIG. 6 device mounted on a patient.
Figure 10:
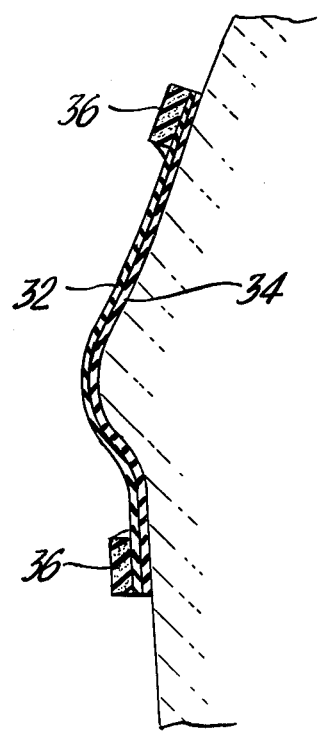
FIG. 10 is a cross-sectional view along the plane 10—10 in FIG. 9 illustrating the conformance of the device to the patient's tissues.

The frame 36 is sized to wrap around the chest so that the end panels 36a and 36b overlap. Releasable fastener strips 38 made of a material such as Velcro are used to fasten the brassiere 30 around the chest of a patient. When fastened onto a patient, the protective film 34 is in contact with the skin and thus may be termed the inner film. Once fastened, as shown in FIG. 9, a vacuum source 40 evacuates air through a tubular member 42. The tube 42 has perforations 44.

The tube 42 extends into the dual film 32, 34 structure and loops through openings 34a in the protective film 34. Thus the tube 42 provides communication, through the perforations 44 with both sides of the protective film 34. That is, certain perforations 44 are in communication with the area between the inner film 34 and the tissue of the patient, while other perforations 44 are in communication with the area between the liquid crystal containing film 32 and the protective film 34. Thus when a vacuum is drawn, air is evacuated from both sides of the inner film 34 causing both films 32 and 34 to conform to the tissues under the brassiere structure 30. In effect, the ambient air pressure acts to force both elastic films 32 and 34 down over and around the tissues being examined and because both films are elastic, both will independently conform to the tissues in the same fashion and for the same reason as does the dual film 16, 20 structure when the box 10 is inflated, as shown in FIG. 5.

The liquid crystal containing film 32 and the protective film 34 are each fastened down by adhesive to the foam rubber frame 36 along the top edge and the two side edges. They are not fastened along the bottom edge and are not fastened to each other at any location over the active surface of the dual film structure except along the length of the perforated tube 42. Thus, air spaces 46 between the two films 32, 34 will exist when the films 32, 34 are in the relaxed state shown in FIG. 6.

The perforated tube 42 is looped through the inner film 34 and thus, when vacuum is drawn, the air in the air spaces 46 will be evacuated and both the liquid crystal containing film 32, as well as the protective film 34, will conform to the patient's tissues. The edges of the two film 32, 34 are not fastened to each other. This assures that during manufacture, air is not trapped between the two films 32 and 34. Air so trapped might expand as the ambient temperature changes when stored and distort the films. Although there will inevitably be air spaces 46 between the two films 32, 34 when in the relaxed position, it is important that the air in these air spaces not be trapped even when in the relaxed state. When a vacuum is drawn through the perforated tube 42, the two highly flexible elastic films 32 and 34 will seal to one another, as they will against the body of the patient, because of the pressure differential and they will be acting in response to that pressure differential much as a flapper valve does.

In both embodiments, the liquid crystal containing film 16 and 32 is about 0.25 mm. thick and the protective film 20 and 34 is also about 0.25 mm, thick. Each of the films 16, 32, 20 and 34 are highly flexible.

In both cases, air spaces 22, 46 exist between the two films and the air in these spaces is drawn or forced out by virtue of a pressure differential between one side of the dual film structure and the other side of the dual film structure. In both cases, the two elastic films are fastened to one another along only their peripheries so that each film is free to stretch and conform to the tissues involved substantially independently of the other film, thereby avoiding puckering of one or the other films. Any such puckering, or failure of both sheets to completely conform to the tissue being investigated, would result in a loss of temperature measurement along the zone of the tissue where the puckering occurs.

What is claimed is:

1. A device for presenting variation in skin temperature comprising:
   a first elastic flexible film carring temperature responsive liquid crystals,
   a second elastic flexible film deployed adjacent said first film to provide a dual film structure,
   said first and second films having a different elastic modulus, said first and second films being attached to one another solely along the periphery thereof, said films having an air space therebetween, and
   pressure means applied to one of the outer surfaces of said dual film structure, when said structure is applied to the patient, to evacuate the air in said air space between said films and to assure conformance of both of said films to the tissue being investigated.

2. The device of claim 1 wherein said second film is substantially more impervious to skin oils than is said first film.

3. The device of claims 1 or 2 wherein a portion of the peripheries of said first and second film are unattached to provide passage of air from said air spaces when said pressure means is applied.

4. The device of claims 1 or 2 wherein said pressure means comprise: means to evacuate air from between said second film and whatever skin tissue said device is placed against and to simultaneously evacuate air from said air spaces between said first and second films.

5. The device of claims 1 or 2 wherein said pressure means comprises: a chamber defined by a frame and said dual film structure, and means to inflate said chamber to cause said dual film structure to stretch out and form a dome over said chamber, said second film being the outer film of said dual film structure.

6. The device of claim 1 further comprising:
   a peripheral frame for supporting said dual film structure and defining a configuration adapted to be placed around the breasts of a woman patient,
   a tubular member having a plurality of openings along a first portion terminating in a first end thereof, the second end of said tubular member adapted to be connected to a vacuum source, at least one of said openings being located in a region spaced from said frame and adapted to be positioned between the breasts and in communication with the outboard surface of said second film, at least another one of said openings being in communication with said air space between said films,
   whereby the evacuation of air from said second end of said tubular member will cause said dual film structure to stretch and conform to the contour of said breasts, said first and second films conforming independently of one another.

7. The device of claim 6 wherein: said peripheral frame is attached to the outboard surface of said liquid crystal containing film.

* * * * *